United States Patent
Boone et al.

(10) Patent No.: US 11,213,690 B2
(45) Date of Patent: Jan. 4, 2022

(54) WAFER LEVEL PACKAGES OF HIGH VOLTAGE UNITS FOR IMPLANTABLE MEDICAL DEVICES

(75) Inventors: Mark R. Boone, Gilbert, AZ (US); Mohsen Askarinya, Chandler, AZ (US); Randolph E. Crutchfield, Scottsdale, AZ (US); Erik J. Herrmann, Mesa, AZ (US); Mark S. Ricotta, Tempe, AZ (US); Lejun Wang, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/524,253

(22) Filed: Jun. 15, 2012

(65) Prior Publication Data

US 2013/0334680 A1  Dec. 19, 2013

(51) Int. Cl.
*H01L 23/48* (2006.01)
*A61N 1/39* (2006.01)
(Continued)

(52) U.S. Cl.
CPC ...... *A61N 1/3956* (2013.01); *H01L 23/49548* (2013.01); *H01L 23/49575* (2013.01); *H01L 25/16* (2013.01); *F04C 2270/041* (2013.01); *H01L 2224/45144* (2013.01); *H01L 2224/45147* (2013.01); *H01L 2224/48091* (2013.01); *H01L 2924/01015* (2013.01); *H01L 2924/01047* (2013.01); *H01L 2924/13055* (2013.01); *H01L 2924/13091* (2013.01)

(58) Field of Classification Search
CPC ......... H01L 2224/97; H01L 2224/2919; H01L 2224/45144; H01L 2224/48137; H01L 21/44; H01L 21/48; H01L 23/498; H01L 23/49575; H01L 23/49584
USPC ........................................................ 257/737
See application file for complete search history.

(56) References Cited

U.S. PATENT DOCUMENTS 5,434,493 A   7/1995 Woody et al.
5,615,091 A   3/1997 Palatnik
(Continued)

OTHER PUBLICATIONS

Wafer Level Stack—WDoD™—Reliable Miniaturization Technologies for Electronics located on-line at http://www.3d-plus.com/techno-wafer-level-stack-wdod.php.
(Continued)

*Primary Examiner* — Phuc T Dang
(74) *Attorney, Agent, or Firm* — Mueting Raasch Group

(57) ABSTRACT

A multi-chip modular wafer level package of a high voltage unit for an implantable cardiac defibrillator includes one or more high voltage (HV) component chips encapsulated with other components thereof in a polymer mold compound of a single reconstituted wafer, wherein all interconnect segments are preferably located on a single side of the wafer. To electrically couple a contact surface of each HV chip, located on a side of the chip opposite the interconnect side of the wafer, the reconstituted wafer may include conductive through polymer vias; alternately, either wire bonds or layers of conductive polymer are formed to couple the aforementioned contact surface to the corresponding interconnect, prior to encapsulation of the HV chips. In some cases one or more of the components encapsulated in the reconstituted wafer of the package are reconstituted chips.

19 Claims, 11 Drawing Sheets

(51) Int. Cl.
*H01L 23/495* (2006.01)
*H01L 25/16* (2006.01)

(56) References Cited

U.S. PATENT DOCUMENTS

| | | | |
|---|---|---|---|
| 5,631,822 | A | 5/1997 | Silberkleit et al. |
| 6,087,922 | A | 7/2000 | Smith |
| 6,094,597 | A | 7/2000 | Wold |
| 6,124,778 | A | 9/2000 | Rowley et al. |
| 6,222,437 | B1 | 4/2001 | Soto et al. |
| 6,278,354 | B1 | 8/2001 | Booth |
| 6,369,685 | B1 | 4/2002 | Milavec et al. |
| 6,420,953 | B1 | 7/2002 | Dadafshar |
| 6,716,672 | B2 | 4/2004 | Val |
| 6,927,663 | B2 | 8/2005 | Iverson et al. |
| 7,120,492 | B2 | 10/2006 | Iverson et al. |
| 7,225,018 | B2 | 5/2007 | Iverson et al. |
| 7,292,126 | B2 | 11/2007 | So |
| 7,375,609 | B2 | 5/2008 | Suzuki et al. |
| 7,476,965 | B2 | 1/2009 | Val et al. |
| 7,635,639 | B2 | 12/2009 | Val et al. |
| 7,877,874 | B2 | 2/2011 | Val |
| 2001/0024838 | A1* | 9/2001 | Ma .............................. 438/106 |
| 2002/0024124 | A1* | 2/2002 | Hashimoto ......... H01L 23/3114 257/678 |
| 2002/0135076 | A1* | 9/2002 | Huang et al. ................. 257/779 |
| 2002/0139990 | A1* | 10/2002 | Suehiro .................. F21V 29/74 257/99 |
| 2002/0185726 | A1* | 12/2002 | North et al. .................. 257/707 |
| 2004/0110323 | A1* | 6/2004 | Becker et al. ................ 438/127 |
| 2005/0107870 | A1 | 5/2005 | Wang et al. |
| 2006/0118934 | A1* | 6/2006 | Ishikawa ............ H01L 25/0657 257/680 |
| 2007/0132079 | A1* | 6/2007 | Otremba ............. H01L 23/3107 257/685 |
| 2009/0102038 | A1 | 4/2009 | Mcelrea et al. |
| 2009/0261468 | A1* | 10/2009 | Kroeninger et al. ......... 257/690 |
| 2010/0012101 | A1 | 1/2010 | Fujinuma et al. |
| 2010/0013101 | A1* | 1/2010 | Hedler et al. ................ 257/773 |
| 2010/0140791 | A1* | 6/2010 | Chen ..................... H01L 23/427 257/712 |
| 2010/0148381 | A1* | 6/2010 | Mahler ................. H01L 21/561 257/794 |
| 2010/0312310 | A1 | 12/2010 | Meskens |
| 2011/0198638 | A1* | 8/2011 | Wang .................... H01L 33/642 257/98 |
| 2013/0335927 | A1 | 12/2013 | Boone |

OTHER PUBLICATIONS

Kwoka et al., Intersil Technical Brief, PCB Land Pattern Design and Surface Mount Guidelines for QFN Packages, Apr. 23, 2009, TB389.6, 9 pages—also located on-line at http://www.intersil.com/data/tb/TB389.pdf.

Boone, "Planar Transformer Assemblies for Implantable Cardioverter Defibrillators", Filed Jun. 15, 2012, U.S. Appl. No. 13/524,222, 13 pages.

Askarinya et al., "Power Sources Suitable for Use in Implantable Medical Devices and Corresponding Fabrication Methods", Filed Jun. 15, 2012, U.S. Appl. No. 13/524,304, 15 pages.

Askarinya, et al., "Integrated Circuit Packaging for Implantable Medical Devices", Filed Jun. 15, 2012, U.S. Appl. No. 13/524,368, 21 pages.

Meyer et al., "System-Integration with eWLB", Electronic System-Integration Technology Conference, 2010, Sep. 13, 2010, 10 pages.

Yonggang et al., "Next Generation eWLB (Embedded Wafer Level BGA) Packaging", 2010 12th Electronics Packaging Technology Conference, Dec. 1, 2010, 8 pages.

(PCT/US2013/035056) PCT Notification of Transmittal of the International Search Report and the Written Opinion of the International Searching Authority, dated Jul. 1, 2013, 13 pages.

U.S. Appl. No. 13/524,368 Notice of Allowance, dated May 7, 2014.

Chinese Office Action, Application No. 201380031166.3, dated May 17, 2016, 7 pages, Chinese language.

Chinese Office Action, Application No. 201380031166.3, dated May 17, 2016, 5 pages, English language.

* cited by examiner

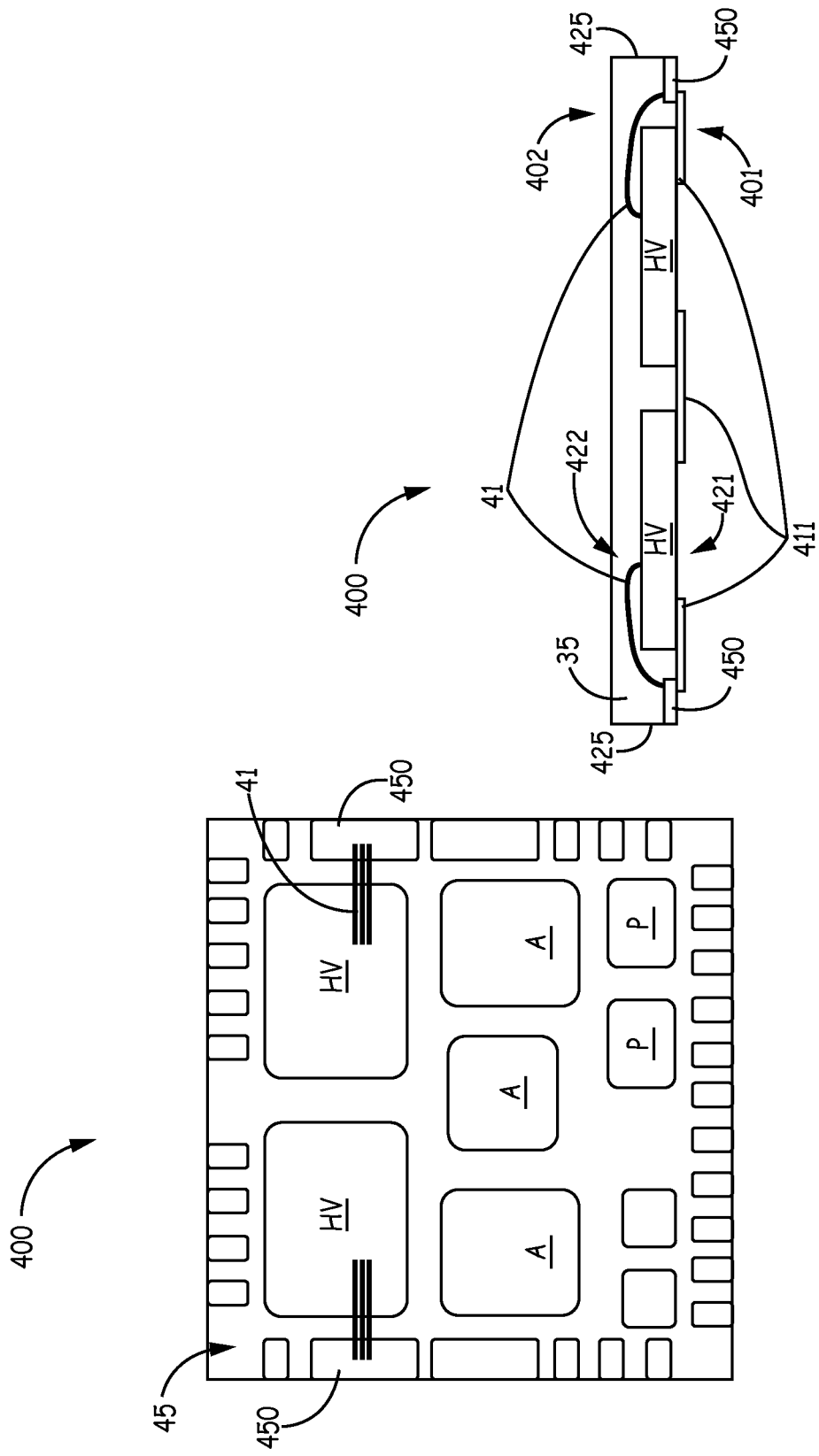

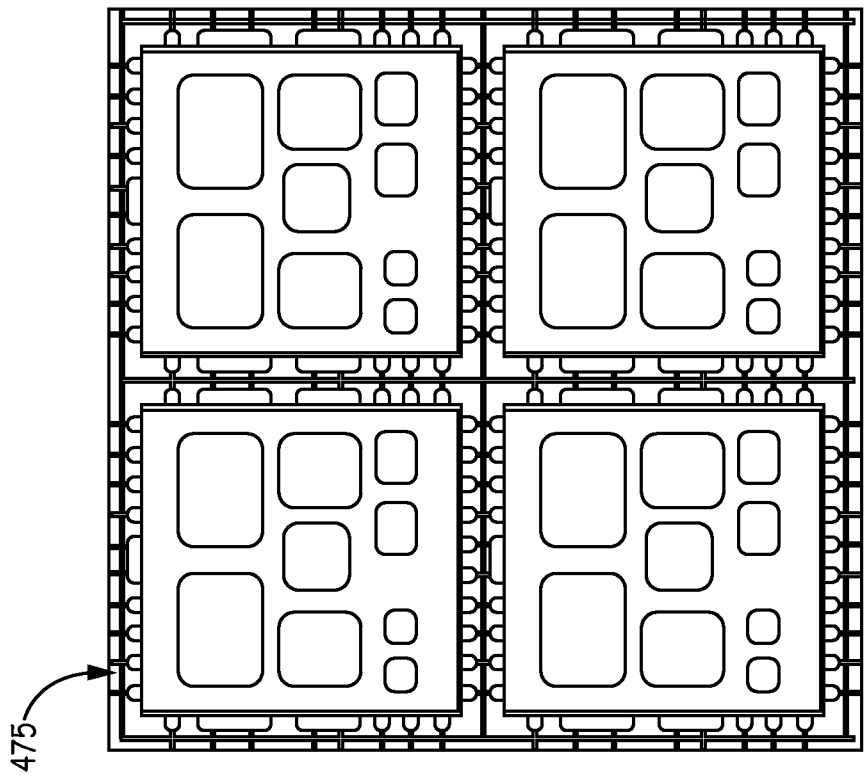
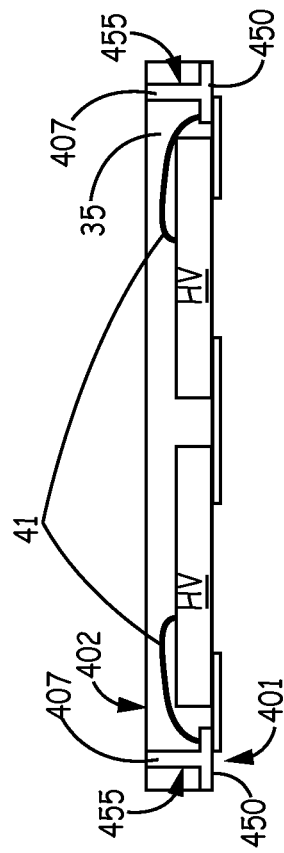

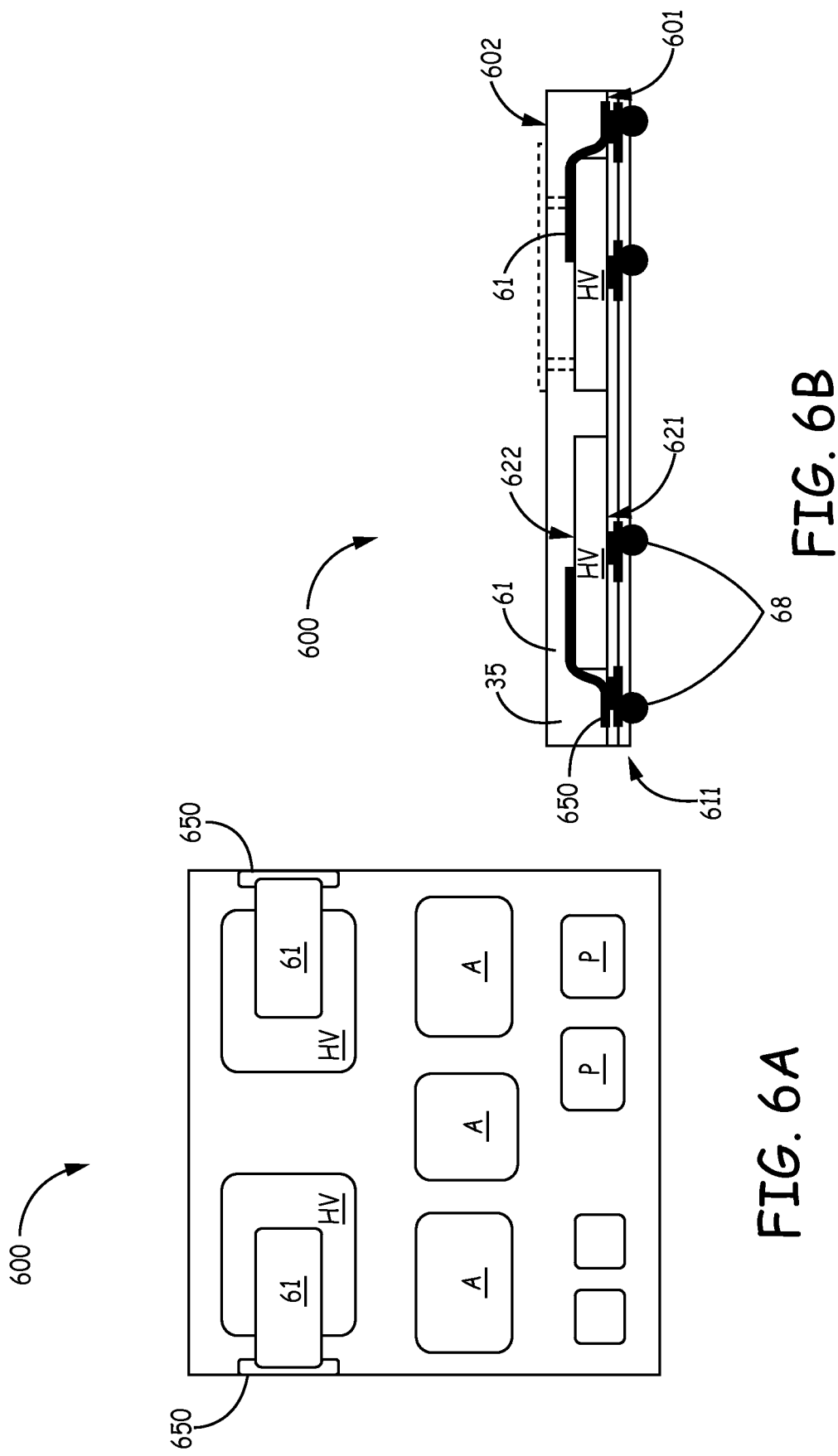

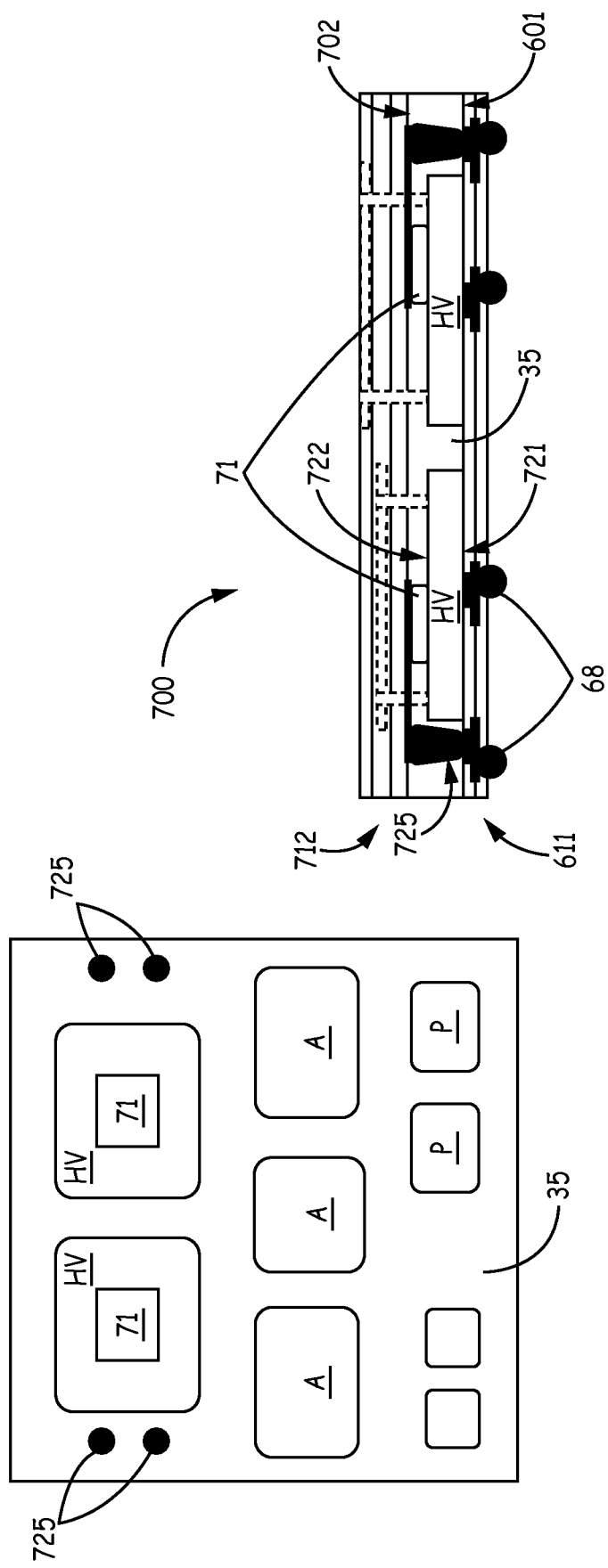

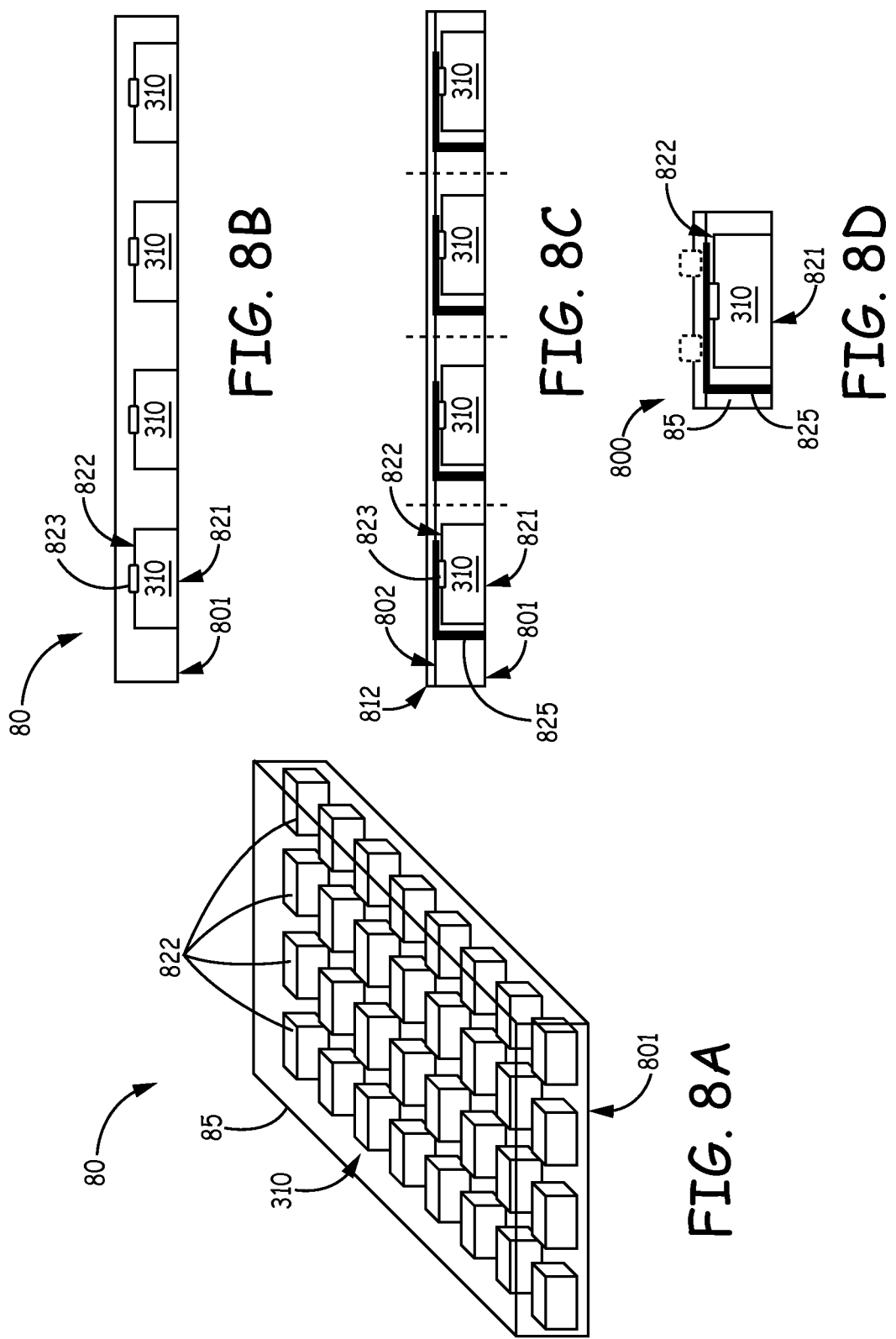

WAFER LEVEL PACKAGES OF HIGH VOLTAGE UNITS FOR IMPLANTABLE MEDICAL DEVICES

CROSS-REFERENCE TO RELATED APPLICATIONS

The present application is related to the following co-pending and commonly-assigned U.S. patent application Ser. Nos. 13/524,368, which is entitled INTEGRATED CIRCUIT PACKAGING FOR IMPLANTABLE MEDICAL DEVICES, filed concurrently herewith; Ser. No. 13/524,304, filed concurrently herewith, which is entitled POWER SOURCES SUITABLE FOR USE IN IMPLANTABLE MEDICAL DEVICES AND CORRESPONDING FABRICATION METHODS; and Ser. No. 13/524,222, which is entitled PLANAR TRANSFORMER ASSEMBLIES FOR IMPLANTABLE CARDIOVERTER DEFIBRILLATORS, filed concurrently herewith.

FIELD OF THE DISCLOSURE

The present invention pertains to electronics packaging, and, more specifically, to wafer level packages of high voltage units suitable for use in implantable medical devices, such as cardiac defibrillators.

BACKGROUND

FIG. 1 is a schematic showing a typical implantable cardiac defibrillator (ICD) 100, which is implanted at a subcutaneous pectoral site in a patient 102, and is, for example, designed to detect ventricular fibrillation and, in response to the detection, to deliver high voltage shock therapy in order to terminate the fibrillation. FIG. 1 illustrates ICD 100 including a hermetically sealed and biocompatible canister 104, for example, formed from a Titanium alloy, which houses a power source and electronic circuitry, and one or more electrical leads 106, which are coupled to the circuitry and extend distally from canister 104, through the venous system 110 and into the heart 108 of patient 102, for example, the right ventricle (RV). Those skilled in the art understand that, for the purpose of monitoring and therapy delivery, the one or more leads 106 include electrodes that are coupled to the ICD circuitry via one or more lead connectors that terminate insulated conductors of the electrodes, at a proximal end of lead(s) 106; the one or more lead connectors are plugged into a connector module 105, which is mounted on canister 104, to make electrical contact with the contained ICD circuitry via hermetically sealed feedthroughs.

FIG. 2 is a simplified circuit diagram of an exemplary high voltage unit included in the ICD circuitry. FIG. 2 illustrates a flyback transformer 240 connected across terminals of a power source 220, a switch 232 connected in series with a primary winding of transformer 240, and a diode 234 connected in series with a secondary winding of transformer 240 across a load, which includes a capacitor element 239 connected by another switch 236 to heart 108, for example, via one or more leads 106 (FIG. 1). FIG. 2 further illustrates a sense circuit 260 that monitors voltage of capacitor element 239, and a controller 210 that receives a signal from the sense circuit 260 to deliver energy from power source 220 when the voltage of capacitor element 239 is below a predetermined threshold. Those skilled in the art will appreciate that a cycling of switch 232 causes transformer 240 to incrementally charge capacitor element 239 to generate voltage on the order of 750 volts or more, so that, when switch 236 is closed, defibrillation shock energy, for example, at a level in the range of 5-40 Joules may be delivered to heart 108.

Those skilled in the art are familiar with emerging wafer level packaging processes that can facilitate a significant downsizing of ICD electronic circuitry like that illustrated in FIG. 2, so that an overall size of the device may be reduced to increase implant comfort. Although many of these packaging processes, which include, for example, redistributed chip packaging (RCP) and wire free die-on-die (WDoD™) stack technology, are known in the art for forming hybrid integrated circuits in relatively thin (planar) wafer level packages, there is still a need for new combinations of these processes directed toward improved configurations of wafer level packages for high voltage units of ICD's.

SUMMARY

A multi-chip modular wafer level package of a relatively compact high voltage unit suitable for a downsized implantable cardiac defibrillator, according to embodiments of the present invention, includes a combination of high voltage (HV) and low voltage (LV) solid-state component chips, and, preferably, corresponding passive components, encapsulated in a polymer mold compound of a single reconstituted wafer. These wafer level packages may be fabricated in batches of uniform and modular packages, wherein individual modular packages, for higher level integration into the HV units of ICD's, are singulated from a reconstituted wafer that encapsulates the batch. Furthermore, state of the art techniques, such as redistributed chip packaging (RCP) processes, may be employed to form a variety of suitable interconnect configurations for components of the modular packages.

According to some preferred embodiments, all interconnect segments for both HV and LV component chips of each modular wafer level package are located on a single side of the reconstituted wafer. The interconnect segments of each modular package may be part of a pre-formed lead frame or 'free-form'. Either wire bonds or layers of conductive polymer are formed, prior to component encapsulation in the polymer mold compound that forms the reconstituted wafer, to electrically couple those contact surfaces of each HV component chip that is located on a side of the chip opposite the interconnect side of the wafer; alternately conductive through polymer vias are formed in the reconstituted wafer, for example, to be employed in combination with routing traces of redistribution layers.

According to some methods of the present invention, a reconstituted wafer is formed around a plurality of the same type of individual solid state component chips, from which individual reconstituted chips are singulated for incorporation in modular wafer level packages, such as those described above. Each reconstituted chip includes a routing trace, for example, formed, prior to singulation, in a redistribution layer that extends over a side of the reconstituted wafer; and, in some embodiments, each reconstituted chip further includes a conductive through polymer via (TPV), for example, also formed prior to singulation, which is coupled to the corresponding routing trace. One or more types of such reconstituted chips can facilitate compact packaging of different thicknesses and combinations of solid state component chips into modular wafer level packages necessary for ICD HV units.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 4A-B are a plan view and a section view, respectively, of portions of an exemplary wafer level package which may correspond to FIG. 2;

FIG. 4C is a plan view of components of a plurality of packages assembled with lead frame-type interconnect elements;

FIG. 4D is a section view a portion of a wafer level package including lead frame-type interconnect elements, according to some embodiments;

FIGS. 6A-B are a plan view and a section view, respectively, of portions of a wafer level package, according to some embodiments;

FIGS. 7A-B are a plan view and a section view, respectively, of portions of a wafer level package, according to some alternate embodiments;

FIG. 8A is a perspective view of a plurality of HV component chips in a reconstituted wafer;

FIG. 8B is a section view of the reconstituted wafer of FIG. 8A, according to some embodiments;

FIG. 8C is a section view of the reconstituted wafer of FIG. 8A, after some processing steps, according to some methods;

FIG. 8D is a section view of a reconstituted component chip, having been diced from the wafer shown in FIG. 8C, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1:
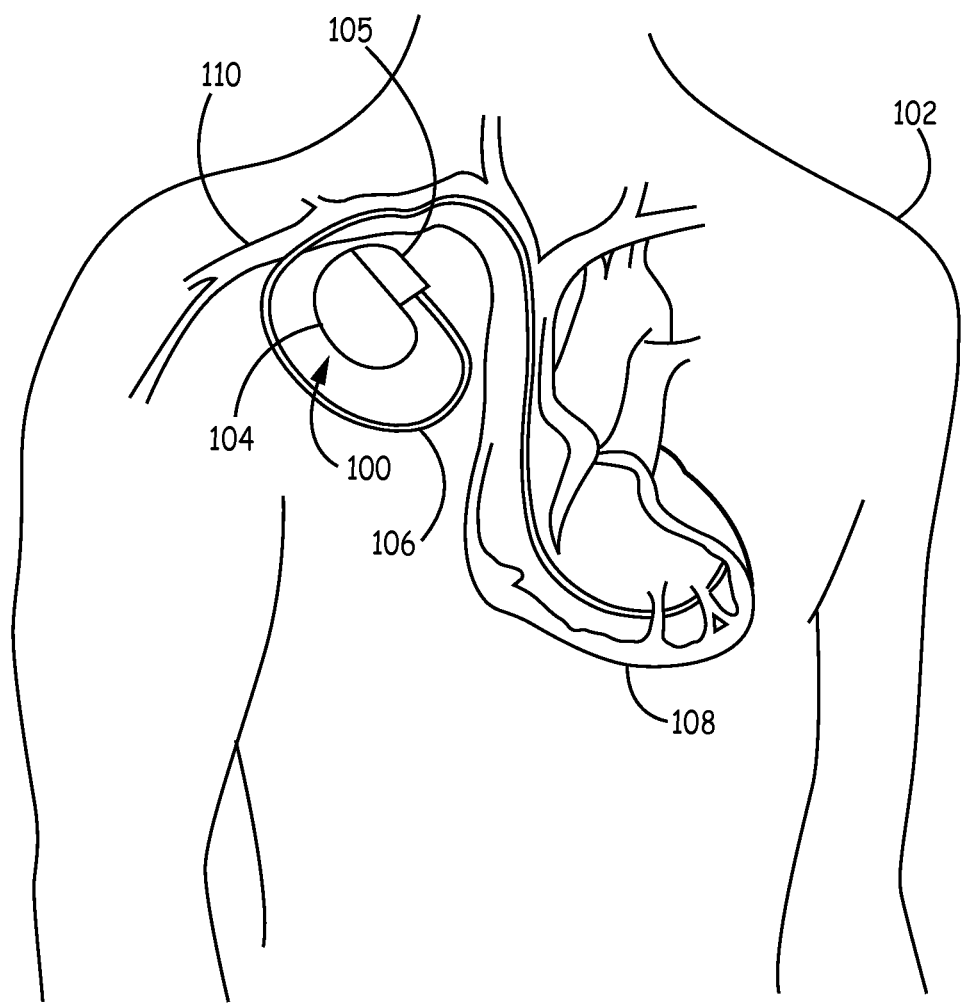
FIG. 1 is a schematic showing a typical placement of an implanted cardiac defibrillator device.
Figure 2:
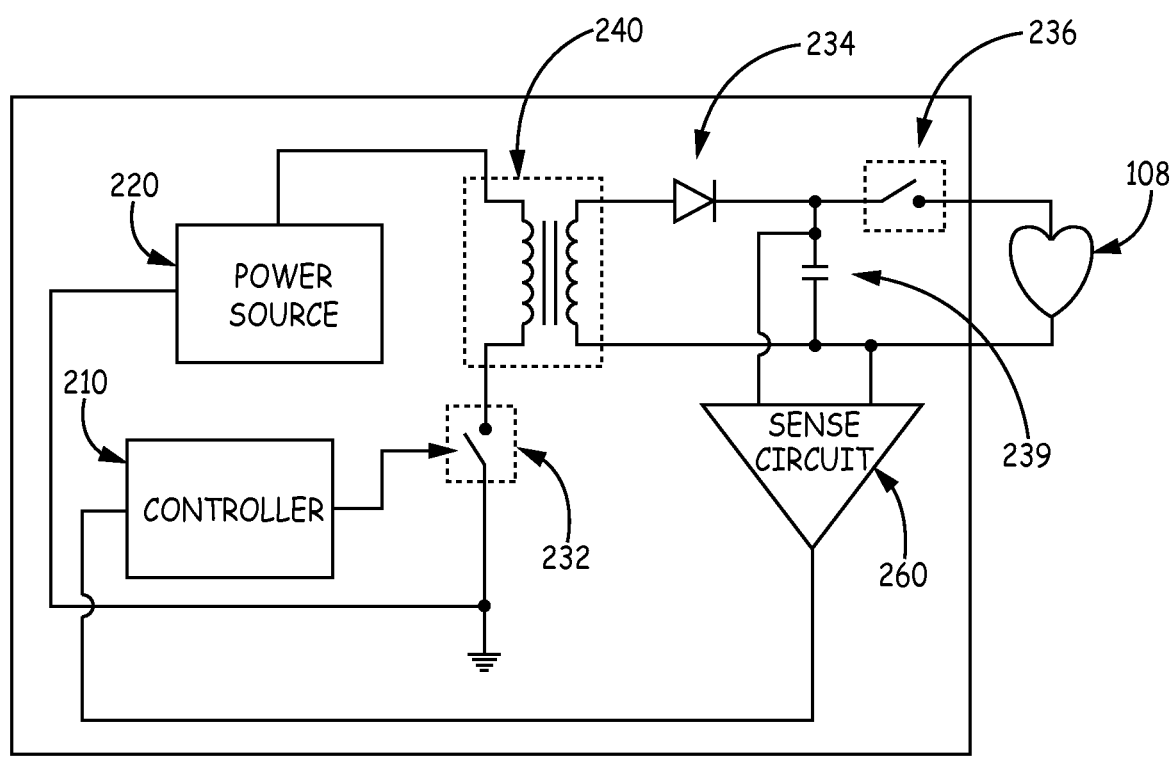
FIG. 2 is a simplified circuit diagram of an exemplary high voltage unit that may be employed by the device shown in FIG. 1.
Figure 3:
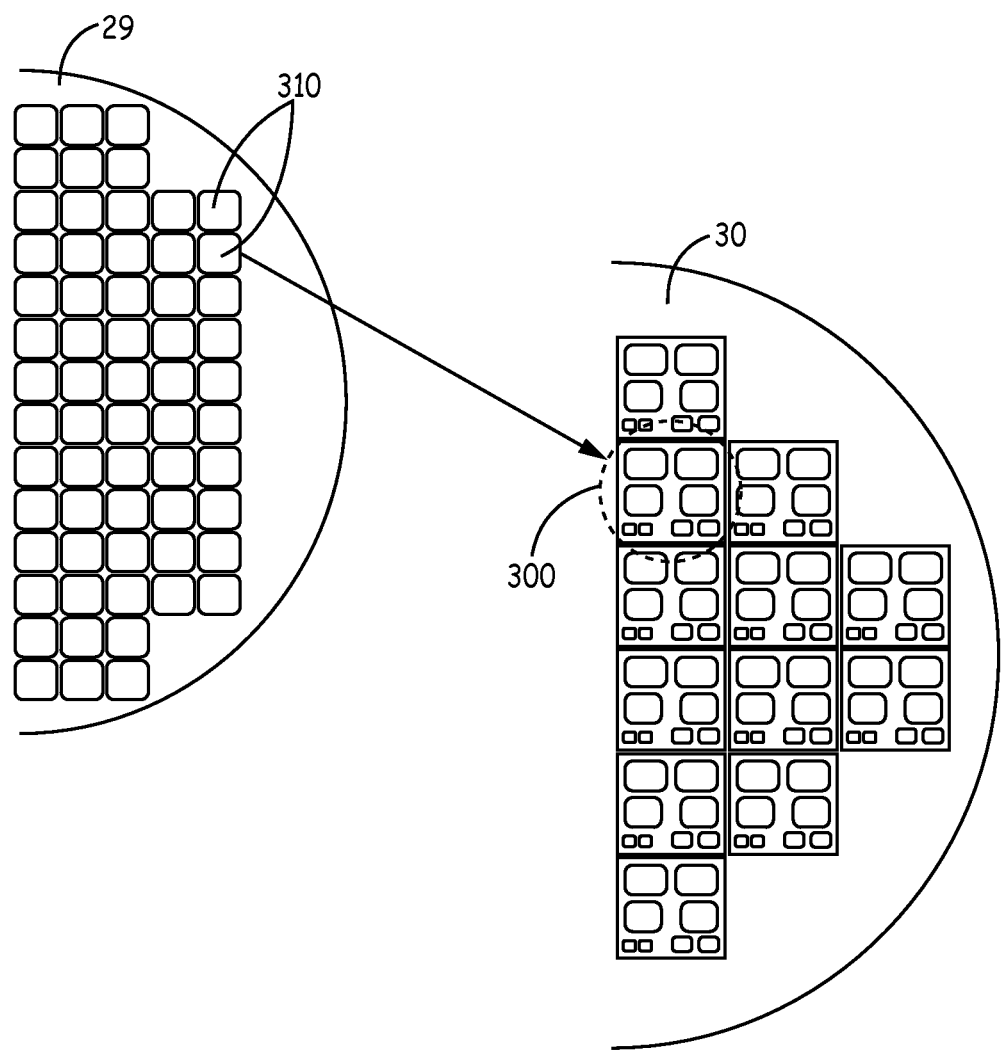
FIG. 3 is a simplified schematic illustrating of a portion of a silicon wafer and a plurality of individual packages in which chips from the wafer are employed.

FIG. 3 is a simplified schematic illustrating of a portion of a silicon wafer 29 and a plurality of individual packages 300, in which active component chips 310 that have been diced from wafer 29, are employed. FIG. 3 further illustrates individual packages 300 having been formed together as a batch in a single reconstituted wafer 30, wherein each package 300 includes at least two high voltage (HV) active component chips 310 along with other, low voltage (LV) active component chips and some passive components, for example, to form an integrated circuit for an ICD HV unit like that illustrated in FIG. 2. After the components of packages 300 are positioned on a release tape, a polymer mold compound (i.e. an epoxy based thermoset including a non-conductive filler such as $AlO_2$ or $SiO_2$, about 80% by volume) encapsulates the components to form reconstituted wafer 30. Alternative embodiments of modular wafer level packages, for example, that are singulated from reconstituted wafer 30 for higher level integration into ICD HV units, will be described in further detail in conjunction with FIGS. 4A-B and following. Each of FIGS. 4A, 6A and 7A show wafer level packages that include some passive components P, for example, capacitors and/or resistors, and a number of active component chips A, two of which are designated as being HV component chips HV, for example, HV power transistors/switches; the remaining component chips A may be HV or LV. According to some exemplary embodiments, each of the illustrated packages preferably has an overall thickness of approximately 0.75 mm. It should be noted that the above referenced co-pending and commonly assigned U.S. patent application Ser. No. 13/524,368, which is hereby incorporated by reference, describes fabrication according to reconstituted wafer and RCP processes of a flyback transformer, which may be included in some embodiments of the present invention.

FIGS. 4A-B are a plan view and a section view, respectively, of portions of an exemplary wafer level package 400. FIGS. 4A-B illustrate package 400 including HV component chips HV, each of which include a first contact surface 421 on a first side thereof and a second contact surface 422, on a second, opposite side thereof. According to the illustrated embodiment, a polymer mold compound 35 encapsulates component chips HV, as well as other chips A and passive components P, to form a reconstituted wafer of package 400, and the first side of each component chip HV is co-planar with a first side 401 of the reconstituted wafer to expose each first contact surface 421, which are solderable surfaces, for example, formed by a gold or silver metallization layer that overlays a nickel barrier layer. FIG. 4B shows each first contact surface 421 exposed between dielectric areas, for example, of spin on epoxy passivation 411, for direct connection to corresponding hybrid substrate interconnects, according to some embodiments.

Figure 4E:
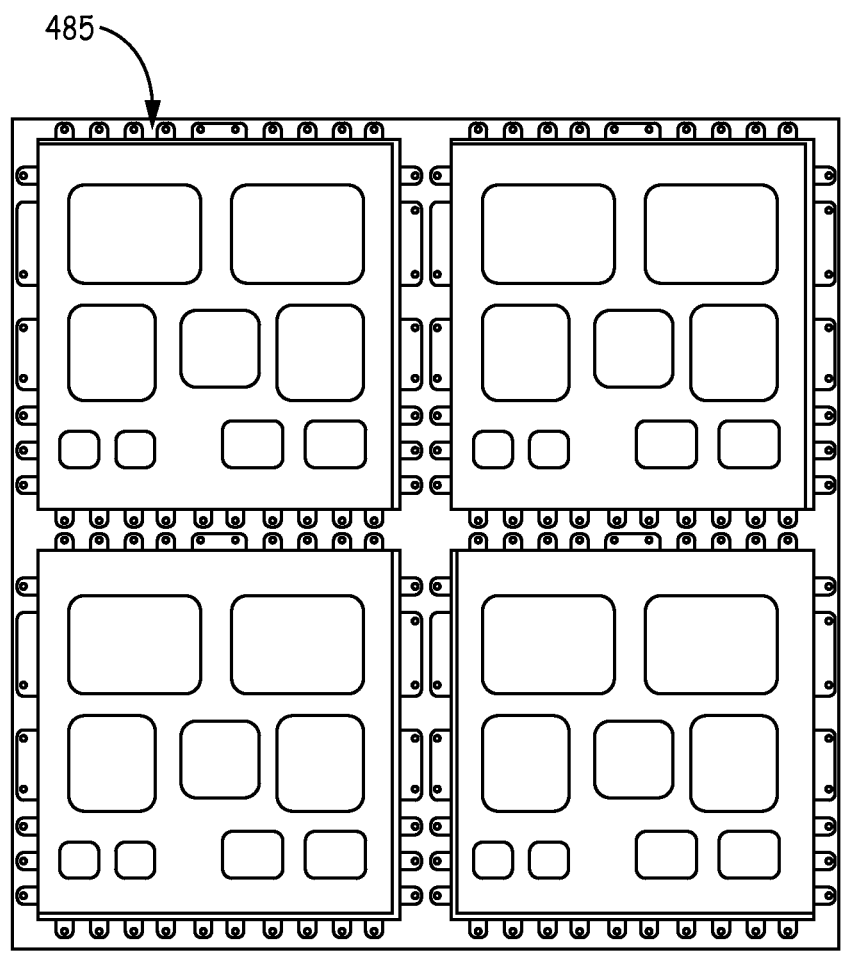
FIG. 4E is a plan view of components of a plurality of packages assembled with an alternate embodiment of interconnect elements.

FIG. 4B further illustrates second contact surfaces 422, each of which is a bondable surface of the corresponding component chip HV, located on a second, opposite side thereof, and a wire bond 41 (i.e. gold or copper wire) coupling each second contact surface 422 to a corresponding interconnect segment 450, which also has a solderable surface exposed at first side 401; wire bonds 41 are formed by methods known in the art, prior to encapsulating component chips HV and segments 450 together in polymer mold compound 35 that forms the reconstituted wafer of wafer level package 400. With reference to FIG. 4A, interconnect segments 450 may be two of a plurality of interconnect segments, which surround a perimeter of the assembled components of package 400 and the pattern of which is pre-formed, either in a lead frame or on an organic substrate, both of which are known in the art and examples of which are shown in FIGS. 4C-E. It should be noted that, for the purpose of simplicity in illustration, details of other component couplings to corresponding interconnect segments of package 400 are omitted.

FIG. 4C illustrates a plurality of interconnect elements held together in a lead frame 475, on which component sets, for example, of four of packages 400, are assembled prior to wire bonding and singulation. Each interconnect element of lead frame 475 may have a flat profile, such that only one surface of each segment is exposed at a side of the reconstituted wafer, for example, like interconnect segments 450 having surfaces exposed at first side 401 in package 400 of FIG. 4B. According to some alternate embodiments, with reference to the section view of FIG. 4D, some or all interconnect elements 455 of lead frame 475 include a vertical element, or conductive post 407, an end of which is exposed at second side 402, for example, following grinding or polishing the reconstituted wafer formed by mold compound 35. According to the illustrated embodiment, the above-described wire bond 41 is formed between each component chip HV and a 'shelf' of the corresponding interconnect element 455, and the exposed end of conductive post 407, at second side 402 may be employed as another solder pad for attaching another component to second side 402 of the wafer. Alternately, a routing trace of a redistribution layer formed over second side 402 may be coupled to conductive post 407, for example, to connect a component contact, which is located second side 402 to an interconnect segment at first side 401, or as will be described for some embodiments below, in conjunction with FIGS. 7A-B.

FIG. 4E illustrates component sets, similar to those shown in FIG. 4C, assembled on an organic substrate-mounted pre-patterned assembly of interconnect elements 485, wherein each element includes a surface and corresponding vias. With reference back to FIGS. 4C-D, it should be noted that the conductive struts of lead frame 475, which hold together the groups of interconnect elements for each package prior to singulation, are cut through when the packages are singulated and then exposed at perimeter edges of the singulated packages, for example, edges 425 of package 400 (FIG. 4B); whereas an entirety of the conductive portion of the pads of pre-patterned assembly 485 shown in FIG. 4E are recessed from the subsequently formed perimeter edges of singulated packages. The recessed interconnect elements enhance the electrical isolation thereof, which may reduce a probability of arcing therebetween, a factor to be considered when packaging high voltage components such as component chips HV. Although the exposure of cut ends of struts of lead frame 475 can make the singulated packages vulnerable to arcing, the employment of lead frame 475 may be preferred for the aforementioned direct connection of first contact surfaces 421 to corresponding hybrid substrate interconnects, which simplifies package 400 and reduce an overall thickness of the HV unit in which wafer level package 400 is employed. Lead frame 475 may also be preferred to decrease a moisture sensitivity level (MSL) of packages 400.

Figure 5:
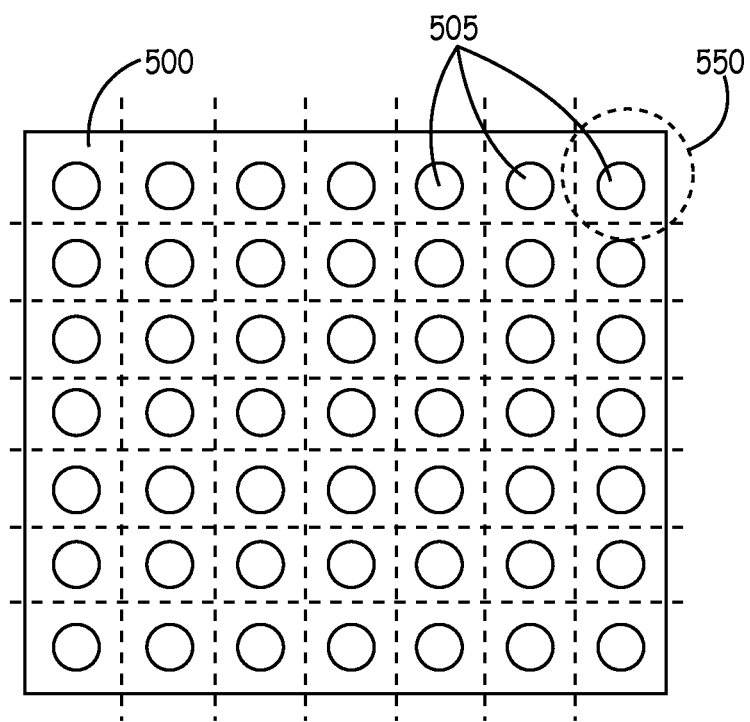
FIG. 5 is a schematic illustrating a plurality of via blocks that may form yet another embodiment of interconnect elements.

FIG. 5 is a schematic illustrating a plurality of via blocks 550, each of which may be employed as an interconnect segment in wafer level package 400, according to some alternate embodiments, for example, to realize the isolation benefit of organic substrate-mounted pre-patterned assembly of interconnect elements 485, as well as the benefit of simplification and thickness reduction offered by lead frame 475. FIG. 5 illustrates a plurality of blind vias 505 formed from a metalized side (i.e. plated with wire bondable gold or Ni—Pd—Au metallization) of a two-sided printed wire board panel 500, wherein the opposite side of panel 500 is preferably formed by an ENIG (Electroless Nickel Immersion Gold) overlay, to which each via 505 is coupled, but could alternately be Ni—Pd—Au metalized. The dashed lines in FIG. 5 represent saw cut lines along which individual via blocks 550 are singulated from the panel, so that individual via blocks 550 may be free-form placed, either in pre-patterned groups or individually, on a release tape (ENIG side down), along with the corresponding components of wafer level packages 400, for subsequent wire bonding (to the metalized side) and polymer encapsulation that leaves the ENIG side of via blocks 550 and first contact surfaces 421 of component chips HV exposed at first side 401, while maintaining electrical isolation between via blocks 550 around perimeter edges 425. Furthermore, using via blocks 550, rather than the above-described lead frame 475 or pre-patterned assembly 485, may allow for more a more rapid and flexible fabrication process.

FIGS. 6A-B are a plan view and a section view, respectively, of portions of a wafer level package 600, according to some embodiments, wherein a conductive polymer is employed rather than wire bonding. Again, only relevant coupling detail for HV component chips HV are shown for the purpose of simplicity in illustration. FIGS. 6A-B illustrate layers of conductive polymer 61 (i.e. conductive epoxy), each of which extends from a corresponding first end thereof, which is coupled to a second contact surface 622 of the corresponding HV component chip HV, to a corresponding second end thereof, which forms a respective interconnect segment 650 at a first side 601 of the reconstituted wafer formed by polymer mold compound 35. According to the illustrated embodiment, layers of conductive polymer 61 are applied after all the components of each package 600 are positioned on the release tape and prior to encapsulation within polymer mold compound 35 to form the reconstituted wafer. A first side of each HV component chip HV is coplanar with first side 601 of polymer mold compound 35 such that a first contact surface 621 of each component chip HV is exposed. In contrast to contact surfaces 421, 422 of components chips HV in package 400 (FIGS. 4A-B), first contact surface 621 of component chip HV in package 600 is a bondable surface and second contact surface 622 is a solderable surface. According to some alternate embodiments, separate interconnect elements, such as via block 550 (FIG. 5), or a lead frame, for example, lead frame 475 (FIG. 4C), may be employed in packages 600, being positioned with components on the release type prior to forming layers of conductive polymer 61, such that the second end of each layer of conductive polymer 61 is coupled to a corresponding interconnect element in proximity to first side 601.

FIG. 6B further illustrates wafer level package 600 including a redistribution layer (RDL) 611 extending over first side 601 of the reconstituted wafer. RDL 611 is formed by an RCP process, known in the art, which successively builds up dielectric layers (i.e. epoxy or polyimide or benzocyclobutene polymer) and conductive routing traces. According to the illustrated embodiment, RDL 611 includes a separate routing trace coupled to each first contact surface 621 and to each interconnect segment 650. The routing traces are isolated from one another by the dielectric of RDL 611, and each routing trace of RDL 611 is shown terminated by a respective bumped bond pad 68, a plurality of which form a ball grid array of each wafer level package 600 for connection to corresponding hybrid substrate interconnects. It should be noted that the routing traces of RDL 611 (as well as those included in additional embodiments, described below) are preferably formed by a thicker than typical plating, for example, 0.002 inch (0.05 mm), in order to carry a relatively high current flow for HV component chips employed in ICD HV units, for example, 50 amps for one to three milliseconds.

FIGS. 7A-B are a plan view and a section view, respectively, of portions of a wafer level package 700, according to some alternate embodiments, wherein a layer of conductive polymer 71 overlays and is coupled to a second contact surface 722 of each HV component chip HV. In package 700, like package 600, a first contact surface 721 of each component chip HV is a bondable surface that is located on the first side of component HV chip, coplanar with first side 601 of polymer mold compound 35 that forms the reconstituted wafer, while second contact surface 722 is a solderable surface on the second, opposite side of component chip HV. According to the illustrated embodiments each layer of conductive polymer 71 is applied to component chips HV prior to encapsulating the components of package 700 in polymer mold compound 35, and then, after mold compound 35 has cured, a grinding and/or polishing step forms a second side 702 of the resulting reconstituted wafer at which layers of conductive polymer 71 are exposed. FIGS. 7A-B illustrate conductive through polymer vias (TPV's) 725 extending through the reconstituted wafer from a first end thereof at first side 601 to a second end thereof at second side 702; each TPV 725 is preferably formed by drilling through-holes and filling the holes with a conductive polymer prior to the grinding and/or polishing to form second side 702. FIG. 7B further illustrates a redistribution layer (RDL) 712, which is formed over second side 702, and which includes routing traces isolated from one another in the dielectric of RDL 712, wherein each routing trace couples a corresponding exposed conductive layer 71 to the second end of the corresponding TPV's 725. With reference back to FIGS. 4C-D, according to alternate embodiments and methods, a lead frame 475 may be employed in lieu of TPV's 725, wherein conductive posts 407 of interconnect elements 455 are exposed at second side 702, by the grinding/polishing step that exposes layers of conductive polymer 71, and each routing trace, of the subsequently formed RDL 712 couples a corresponding exposed conductive layer 71 to the exposed end of the corresponding post 407.

With further reference to FIG. 7A, a pair of TPV's 725 (or conductive posts 407 of one or more of the above described interconnect elements 455) is employed for each component chip HV, for example to reduce resistance and increase current handling capability for a given diameter and length of each TPV 725. Multiple TPV's 725 for each component chip HV can also provide redundancy to increase fabrication yield and reliability. Like package 600, package 700 includes RDL 611 in which separate, isolated routing traces are coupled to each of first contact surfaces 721 and to each interconnect segment formed by the corresponding first ends of TPV's 725, and are terminated by bump bond pads 68.

With further reference to FIG. 7B, dashed lines illustrate optional heat sink assemblies of package 700. Each heat sink assembly includes an array of heat pipes extending outward from the second side of each component chip HV to couple with a corresponding heat sink plate formed in RDL 712. The arrays of heat pipes may be formed by blind copper plated vias, and the heat sink plates by copper metallization. Each heat sink plate preferably has a surface area equal to or greater than that of the corresponding component chip HV and a thickness between approximately 7 micrometers and approximately 14 micrometers. Although FIG. 7B illustrates the heat sink plates located in different sub-layers of RDL 712, for example, to assure electrical isolation therebetween, in alternate embodiments different heat sink plates may be located in the same sub-layer of RDL 712. Furthermore, with reference back to FIG. 6B, package 600 may include a heat sink assembly for each of component chips HV (one is shown with dashed lines), wherein an array of heat pipes extends through polymer mold compound 35 from the second side of each component chip HV to a corresponding heat sink plate formed over second side 602 of the wafer. Each heat pipe for package 600 may be formed by a blind plated via formed following encapsulation within mold compound 35, or by columns of stacked gold stud bumps mounted on the second side of each component chip HV prior to encapsulation.

FIG. 8A is a perspective view of a plurality of active component chips 310, for example, having been diced from silicon wafer 29 shown in FIG. 3. FIG. 8A illustrates component chips 310 encapsulated in a polymer mold compound 85 to form a reconstituted wafer 80, wherein a first side of each chip 310 is coplanar with a first side 801 of wafer 80 so that a first contact surface 821 of each chip 310 is exposed, as illustrated in the section view of FIG. 8B. FIG. 8B further illustrates a second contact surface 802 of each chip 310 overlaid with a conductive protrusion, or crest 823, for example, formed by a layer of a conductive epoxy or gold ball bumps. According to the illustrated embodiment, each conductive crest 823 preferably has a thickness of approximately 25 micrometers, so that wafer 80 may be thinned, by a mechanical grinding or polishing process, to expose conductive crest 823 of each chip 310 at a second side 802 thereof (FIG. 8C) without risk of damaging chips 310. However, according to some alternate embodiments and methods, in lieu of conductive crests 823, wafer is thinned to within approximately 25 micrometers from second contact surfaces 822 of chips 310, and then a plurality of conductive vias are formed from second side 802 of wafer 80, such that each extends to a corresponding second contact surface 822.

Figure 9A:
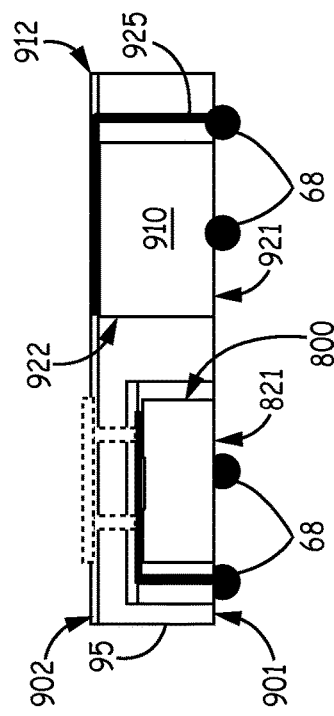
FIGS. 9A-C are section views of portions of wafer level packages that employ one or more reconstituted chips, according to additional alternate embodiments.
Figure 9C:
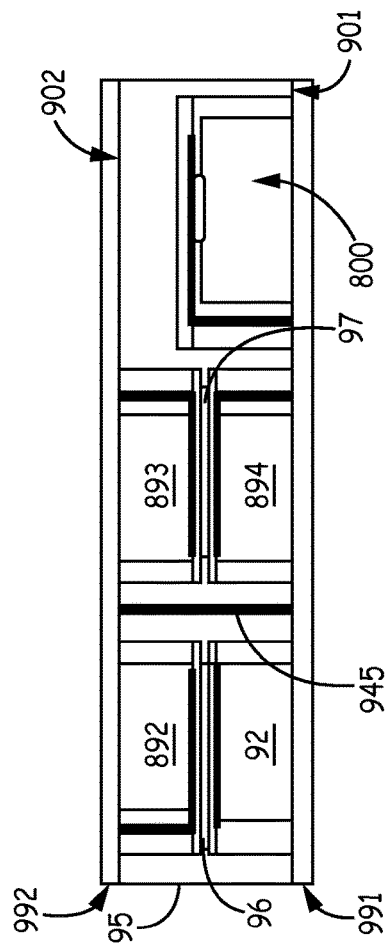
Figure 9B:
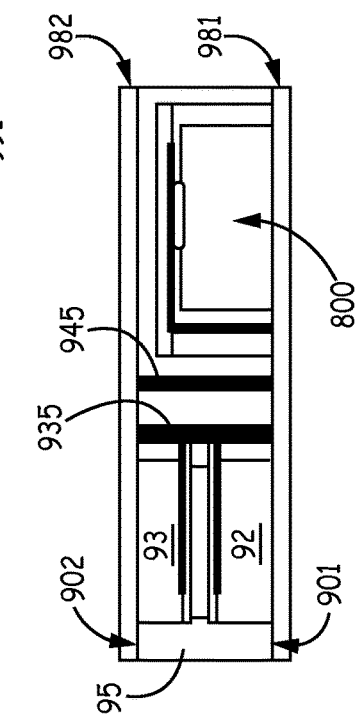

FIG. 8C is a section view through wafer 80 following thinning and RCP processing steps, and following subsequent formation of a through polymer via (TPV) 825 alongside each chip 310. Each conductive crest 823 (or via) is exposed at second side 802 of thinned wafer 80, so that second contact surface 822 of each chip 310 can be coupled to a corresponding routing trace of a redistribution layer (RDL) 812. According to the illustrated embodiment, each TPV 825 is formed, from first side 801 of wafer 80, to extend from first side 801 to the corresponding routing trace, so that each second contact surface 822 has an interconnect at the end of TPV 825 which is coplanar with first side 801 of wafer. FIG. 8D is a section view of a reconstituted component chip 800 diced from wafer 80, for example, along dashed lines of FIG. 8C. According to some embodiments, reconstituted chip 800 is an HV component chip that may be combined with other active and passive components in a wafer level package for an ICD HV unit, for example, as a substitute for one or both of component chips HV in package 700 of FIGS. 7A-B. FIGS. 9A-C are section views of portions of additional alternate embodiments of wafer level packages that include one or more reconstituted chips encapsulated within reconstituted wafers.

FIG. 9A illustrates reconstituted chip 800 encapsulated, along with another, thicker component chip 910, within a polymer mold compound 95 that forms a reconstituted wafer having a first side 901 and a second, opposite side 902. According to the illustrated embodiment, first contact surfaces 821, 921 are exposed at first side 901 of the reconstituted wafer, and the reconstituted wafer has been thinned, for example, by grinding and/or polishing methods known in the art, to form second side 902 thereof, for example, at which a conductive crest of second contact surface 922 of the thicker component chip 910 is exposed. Alternately, in lieu of a conductive crest, a conductive via is formed through a thickness (i.e. approximately 25 micrometers) of polymer mold compound 95, from second side 902 to second contact surface 922 of chip 910.

Following the thinning, a redistribution layer (RDL) 912 is formed with a routing trace coupled to second contact surface 922. FIG. 9A further illustrates a through polymer via (TPV) 925 extending alongside component chip 910, from a first end thereof at first side 901, to a coupling with the routing trace of RDL 912, so that the first end of TPV 925 forms an interconnect segment for second contact surface 922 of component chip 910 at first side 901. With further reference to FIG. 9A, bumped bond pads 68 may be part of a ball grid array of the reconstituted wafer for connection to corresponding hybrid substrate interconnects. According to an exemplary embodiment, component chips 910, 800 are different voltage-controlled transistors, for example, component chip 910 being a 1200 volt IGBT, and reconstituted chip 800 being a 60 volt MOSFET.

Dashed lines in FIG. 9A correspond to an option heat sink assembly wherein an array of heat pipes extends through polymer mold compound 95 from reconstituted chip 800 to a corresponding heat sink plate formed over second side 902 of the reconstituted wafer. Each heat pipe may be formed by a blind plated via formed following encapsulation within mold compound 95, or by columns of stacked gold stud bumps mounted on the second side of reconstituted chip, as shown with dashed lines in FIG. 8D, prior to encapsulation. Although not shown, another heat sink assembly may be provided for component chip 910 within additional, overlaying sub-layers of RDL 912.

FIG. 9B illustrates a reconstituted wafer formed by polymer mold compound 95 that encapsulates reconstituted chip 800 together with a stacked pair of component chips 92, 93, according to some alternate embodiments. Component chips 92, 93, are preferably reconstituted chips, that are pre-packaged with a redistribution layer including a routing trace which forms a backside of each reconstituted chip. The routing trace of each chip 92, 93 is electrically coupled to a respective contact surface, and the backsides of chips 92, 93 are bonded together, with either a conductive or non-conductive adhesive (i.e. epoxy), prior to encapsulation in polymer mold compound 95 to form the illustrated reconstituted wafer. Following encapsulation, the reconstituted wafer is thinned to a second side 902 thereof, for example, to expose a conductive crest of a contact surface/terminal of chip 93, located opposite the backside thereof, and a TPV 935 is formed through the reconstituted wafer to electrically connect the routing traces of chips 92, 93 together. FIG. 9B further illustrates the reconstituted wafer including redistribution layers 981, 982 formed over respective sides 901, 902 thereof, wherein RDL 981 includes routing traces to couple each contact terminal and interconnect segment for each chip 92, 93, 800 to a corresponding bumped bond pad of a ball grid array (i.e. for connection to corresponding hybrid substrate interconnects), and RDL 982 includes routing traces that couple contact terminals of chip 93 to other, corresponding TPV's (shown by a representative TPV 945) that each extend from second side 902 to interconnect segment ends thereof located at first side 901.

FIG. 9C illustrates another reconstituted wafer formed by polymer mold compound 95 that encapsulates reconstituted chip 800 together with a first stacked pair of component chips 92, 892 and a second stacked pair of component chips 893 and 894. According to the illustrated embodiment, each of component chips 892, 893 and 894 are reconstituted chips having been formed in the same manner as reconstituted chip 800. FIG. 9C further illustrates the backsides of chips 92, 892 bonded together, for example, with a conductive adhesive (i.e. epoxy) 96, wherein each of chips 92 and 892 may be high voltage (HV) chips sharing a common backside connection; whereas the backsides of chips 893, 894 are bonded together with a non-conductive adhesive (i.e. epoxy) 97, and each of chips 893, 894 may be low voltage (LV) chips having backside connections isolated from one another. Following encapsulation of stacked chips 892 and 92, 893 and 894, and of chip 800, the reconstituted wafer is thinned to second side 902, for example, at which a conductive crest of a contact terminal of each of chips 892 and 893 is exposed, or at which, according to some alternate embodiments and methods, in lieu of conductive crests, a plurality of conductive vias are formed through a thickness (i.e. approximately 25 micrometers) of polymer mold compound 95 to the corresponding contact terminal (not shown). TPV's, for example, as illustrated by representative TPV 945, are formed through polymer mold compound 95, after which each redistribution layer (RDL) 991, 992 is formed. Each RDL 991, 992 may include routing traces, as described above, wherein the routing traces of RDL 992 couple contact terminals of chips 892, 893, in proximity to second side 902 of the reconstituted wafer, to corresponding TPV's, which provide corresponding interconnect segments on first side 901 of the wafer, and the routing traces of RDL 991 couple each contact terminal and interconnect segment to a corresponding bumped bond pad of a ball grid array.

In the foregoing detailed description, the invention has been described with reference to specific embodiments. However, it may be appreciated that various modifications and changes can be made without departing from the scope of the invention as set forth in the appended claims.

The invention claimed is:

1. A multi-chip modular wafer level package of a high voltage unit for an implantable cardiac defibrillator, the package comprising:
 a high voltage (HV) component chip including a first conductive contact surface located on a first side thereof, and a second conductive contact surface located on a second side thereof, the second side of the HV chip being opposite the first side of the HV chip;
 an interconnect coupled to the second conductive contact surface of the HV chip, wherein the interconnect comprises:
  an interconnect segment; and
  a conductive coupling extending between the second conductive contact surface of the HV chip to the interconnect segment to electrically couple the second conductive contact surface of the HV chip to the interconnect segment; and
 a reconstituted wafer formed by a polymer mold compound in which the HV chip is encapsulated together with other chips of the multi-chip modular wafer level package, wherein the polymer mold compound forming the reconstituted wafer fully encapsulates the conductive coupling of the interconnect and encapsulates the HV chip and the other chips such that the first side of each chip is coplanar with a first side of the wafer, and wherein the polymer mold compound forming the reconstituted wafer encapsulates the HV chip and the other chips such that the second side of the HV chip coupled to the interconnect is enclosed within the polymer mold compound,
 wherein at least a portion of the interconnect coupled to the second conductive contact surface located on the second side of the HV chip is encapsulated within the polymer mold compound used to form the reconstituted wafer and the interconnect segment provides an interconnect segment contact surface at the first side of the wafer.

2. The package of claim 1, wherein the interconnect comprises a layer of conductive polymer extending from a first end, coupled to the second conductive contact surface of the HV chip, to a second end defining the conductive coupling and forming the interconnect segment at the second end, the layer of conductive polymer being encapsulated within the mold compound such that the second end thereof forms the interconnect segment contact surface provided at the first side of the wafer.

3. The package of claim 2, further comprising a redistribution layer extending over the first side of the reconstituted wafer, the redistribution layer comprising a plurality of routing traces, a first of the routing traces being coupled to the first conductive contact surface of the HV component chip and a second of the routing traces being coupled to the interconnect segment contact surface provided at the first side of the wafer.

4. The package of claim 1, further comprising a redistribution layer extending over the first side of the reconstituted wafer, the redistribution layer comprising a plurality of routing traces, a first of the routing traces being coupled to the first conductive contact surface of the HV component chip and a second of the routing traces being coupled to the interconnect segment contact surface provided at the first side of the wafer.

5. The package of claim 1, further comprising:
a layer of conductive polymer of the interconnect overlaying and coupled to the second conductive contact surface of the HV component chip; and
a redistribution layer extending over a second side of the reconstituted wafer, the second side of the reconstituted wafer being opposite the first side thereof, the redistribution layer comprising a routing trace of the interconnect coupled to the layer of conductive polymer; and
wherein the reconstituted wafer includes a conductive through polymer via (TPV) of the interconnect extending from a first end at the first side of the wafer to a second end at the second side of the wafer, the second end of the TPV being coupled to the conductive routing trace of the redistribution layer, and the HV interconnect segment comprising the first end of the TPV.

6. The package of claim 5, further comprising another redistribution layer extending over the first side of the reconstituted wafer, the other redistribution layer comprising a plurality of routing traces, a first of the routing traces being coupled to the first conductive contact surface of the HV component chip and a second of the routing traces being coupled to the interconnect segment contact surface provided at the first side of the wafer.

7. The package of claim 1, wherein the interconnect comprises a via block.

8. The package of claim 1, wherein the interconnect further comprises a conductive post extending from the interconnect segment to a second side of the reconstituted wafer, the second side of the reconstituted wafer being opposite the first side thereof.

9. The package of claim 8, further comprising:
a layer of conductive polymer of the interconnect overlaying and coupled to the second conductive contact surface of the HV component chip; and
a redistribution layer extending over a second side of the reconstituted wafer, the second side of the reconstituted wafer being opposite the first side thereof, the redistribution layer comprising a routing trace of the interconnect coupling the layer of conductive polymer to the conductive post of the interconnect.

10. The package of claim 1, wherein:
the HV chip is incorporated in a reconstituted chip, the reconstituted chip further comprising:
a first side corresponding to and coplanar with the first side of the HV chip;
a second side corresponding to the second side of the HV chip;
a conductive through polymer via (TPV) of the interconnect extending from a first end, at the first side of the reconstituted chip, to a second end, at the second side of the reconstituted chip; and
a routing trace of the interconnect extending over the second side of the reconstituted chip and coupling the second conductive contact surface of the HV chip to the second end of the TPV; and
the interconnect segment comprises the first end of the TPV of the reconstituted chip.

11. The package of claim 10, further comprising:
another HV component chip encapsulated in the reconstituted wafer and having a thickness greater than that of the reconstituted chip, the other HV component chip including a first conductive contact surface located on a first side thereof, and a second conductive contact surface located on a second side thereof, the second side of the other HV component chip being opposite the first side of the other HV component chip, the first conductive contact surface of the other HV component chip being coplanar with the first side of the reconstituted wafer, and the second conductive contact surface of the other HV component chip being coplanar with a second side of the reconstituted wafer, the second side of the reconstituted wafer being opposite the first side; and
a redistribution layer extending over the second side of the reconstituted wafer, the redistribution layer comprising a routing trace coupled to the second conductive contact surface of the other HV component chip; and
wherein the reconstituted wafer includes a conductive through polymer via (TPV) extending alongside the other HV component chip, from a first end at the first side of the wafer to a second end at the second side of the wafer, the first end of the TPV forming an interconnect segment for the other HV component chip, and the second end of the TPV being coupled to the routing trace of the redistribution layer.

12. The package of claim 10, further comprising:
a stacked pair of reconstituted chips encapsulated in the reconstituted wafer, each reconstituted chip of the stacked pair comprising a first side, a first conductive contact surface located on the first side, a second, opposite side, a second conductive contact surface located on the second side, and a routing trace extending over the corresponding second side and being coupled to the corresponding second conductive contact surface; and
wherein the first conductive contact surface of a first reconstituted chip of the stacked pair is coplanar with the first side of the reconstituted wafer, and the first conductive contact surface of a second reconstituted chip of the stacked pair is coplanar with the second side of the reconstituted wafer; and
the reconstituted wafer includes a conductive through polymer via (TPV) extending alongside the stacked pair, from a first end at the first side of the wafer to a second end at the second side of the wafer, the TPV coupling together the routing traces that extend over the second sides of the stacked pair of reconstituted chips.

13. The package of claim 10, further comprising:
a stacked pair of reconstituted chips encapsulated in the reconstituted wafer, a first reconstituted chip of the stacked pair comprising a first side, a first conductive contact surface located on the first side, a second, opposite side, a second conductive contact surface located on the second side, and a routing trace extending over the second side and being coupled to the corresponding second conductive contact surface, and a second reconstituted chip of the stacked pair comprising a first side, a first conductive contact surface located on the first side of the second reconstituted chip, a second side, a second conductive contact surface located on the second side of the second reconstituted chip, a through polymer via (TPV) extending from a first end, at the first side of the second reconstituted chip, to a second end, at the second side of the second reconstituted chip, and a routing trace extending over the second side of the second reconstituted chip and coupling the second conductive contact surface of the second reconstituted chip to the second end of the TPV of the second reconstituted chip; and
a conductive adhesive adhering the second sides of the stacked pair of reconstituted chips together to conductively couple the routing traces thereof; and
wherein the first conductive contact surface of the first reconstituted chip of the stacked pair is coplanar with the first side of the reconstituted wafer, and the first conductive contact surface of the second reconstituted chip of the stacked pair is coplanar with the second side of the reconstituted wafer.

14. The package of claim 10, further comprising:
a stacked pair of reconstituted chips encapsulated in the reconstituted wafer, a first reconstituted chip of the stacked pair comprising a first side, a first conductive contact surface located on the first side, a second, opposite side, a second conductive contact surface located on the second side, a through polymer via (TPV) extending from a first end, at the first side, to a second end, at the second side, and a routing trace extending over the second side and coupling the second conductive contact surface to the second end of the TPV, and a second reconstituted chip of the stacked pair comprising a first side, a first conductive contact surface located on the first side of the second reconstituted chip, a second side, a second conductive contact surface located on the second side of the second reconstituted chip, a through polymer via (TPV) extending from a first end, at the first side of the second reconstituted chip, to a second end, at the second side of the second reconstituted chip, and a routing trace extending over the second side of the second reconstituted chip and coupling the second conductive contact surface of the second reconstituted chip to the second end of the TPV of the second reconstituted chip; and
a non-conductive adhesive adhering the second sides of the stacked pair of reconstituted chips together; and
wherein the first conductive contact surface of the first reconstituted chip of the stacked pair is coplanar with the first side of the reconstituted wafer, and the first conductive contact surface of the second reconstituted chip of the stacked pair is coplanar with the second side of the reconstituted wafer.

15. The package of claim 10, further comprising:
a redistribution layer extending over a second side of the reconstituted wafer, the second side of the wafer being opposite the first side thereof; and
a heat sink plate extending within or over the redistribution layer;
wherein the second side of the reconstituted chip is recessed from a second side of the reconstituted wafer; and
the reconstituted wafer includes an array of heat pipes formed therein and extending from the second side of the reconstituted chip to the heat sink plate.

16. The package of claim 10, further comprising:
a redistribution layer extending over a second side of the reconstituted wafer, the second side of the wafer being opposite the first side thereof; and
a heat sink plate extending within or over the redistribution layer;
wherein the second side of the reconstituted chip is recessed from a second side of the reconstituted wafer; and
the reconstituted chip further comprises an array of columns of stacked gold stud bumps mounted on the second side of reconstituted chip and extending to the heat sink plate.

17. The package of claim 1, further comprising at least one dielectric area positioned on one or both of the first side of the HV chip and the first side of the wafer at least between the interconnect segment and the HV chip to reduce a probability of arcing between the interconnect segment and the first conductive surface, wherein the at least one dielectric portion defines at least one opening to expose the first conductive contact surface.

18. A multi-chip modular wafer level package of a high voltage unit for an implantable cardiac defibrillator, the package comprising:
a high voltage (HV) component chip including a first conductive contact surface located on a first side thereof, and a second conductive contact surface located on a second side thereof, the second side of the HV chip being opposite the first side of the HV chip;
a reconstituted wafer formed by a polymer mold compound in which the HV chip is encapsulated together with other chips of the package, such that the first side of each chip is coplanar with a first side of the wafer;
an interconnect coupled to the second conductive contact surface of the HV chip, wherein the interconnect comprises:
an interconnect segment located on the first side of the wafer; and
a conductive coupling extending between the second conductive contact surface of the HV chip to the interconnect segment to electrically couple the second conductive conduct surface of the HV chip to the interconnect segment, wherein the polymer mold compound forming the reconstituted wafer fully encapsulates the conductive coupling of the interconnect; and
a heat sink plate extending over a second side of the reconstituted wafer, the second side of the reconstituted wafer being opposite the first side thereof, wherein the heat sink plate comprises a first side and a second side opposite the first side facing the second side of the HV chip, wherein the heat sink plate is separated from the second side of the HV chip by at least the polymer mold compound; and wherein:

the second side of the HV chip is recessed from the second side of the reconstituted wafer; and the reconstituted wafer includes an array of heat pipes formed therein, wherein each heat pipe of the array of heat pipes extends from a first end adjacent the second side of the HV chip and terminates at a second end adjacent the second side of the heat sink plate, wherein all structure of each of the heat pipes of the array of heat pipes extends vertically through at least the polymer mold compound from the second side of the HV chip to the heat sink plate.

19. A multi-chip modular wafer level package of a high voltage unit for an implantable cardiac defibrillator, the package comprising:

a high voltage (HV) component chip including a first contact surface located on a first side thereof, and a second contact surface located on a second side thereof, the second side of the HV chip being opposite the first side of the HV chip;

a reconstituted wafer formed by a polymer mold compound in which the HV chip is encapsulated together with other chips of the package, such that the first side of each chip is coplanar with a first side of the wafer;

an interconnect coupled to the second contact surface of the HV chip, wherein the interconnect comprises:

an interconnect segment located on the first side of the wafer; and a conductive coupling extending between the second contact surface of the HV chip to the interconnect segment to electrically couple the second contact surface of the HV chip to the interconnect segment, wherein the polymer mold compound forming the reconstituted wafer fully encapsulates the conductive coupling of the interconnect; and a heat sink plate extending over a second side of the reconstituted wafer, the second side of the reconstituted wafer being opposite the first side thereof, wherein the heat sink plate comprises a first side and a second side opposite the first side facing the second side of the HV chip, wherein the heat sink plate is separated from the second side of the HV chip by at least the polymer mold compound; and wherein:

the second side of the HV chip is recessed from the second side of the reconstituted wafer; and the reconstituted wafer further includes an array of columns of stacked gold stud bumps mounted on the second side of the HV chip, wherein each column of the array of columns extends from a first end adjacent the second side of the HV chip and terminates at a second end adjacent the second side of the heat sink plate, wherein all structure of each of the columns of the array of columns extends vertically through at least the polymer mold compound to the heat sink plate.

* * * * *